US009527818B2

(12) United States Patent
Kikuchi et al.

(10) Patent No.: US 9,527,818 B2
(45) Date of Patent: Dec. 27, 2016

(54) METHOD FOR PRODUCING SULFONYL AMIDINE COMPOUND

(71) Applicant: Astellas Pharma Inc., Tokyo (JP)

(72) Inventors: Takashi Kikuchi, Tokyo (JP); Shinya Yoshida, Tokyo (JP); Atsushi Nakamura, Tokyo (JP); Takahiro Akiba, Tokyo (JP); Toshitaka Yoshino, Tokyo (JP); Shuichi Nakagawa, Tokyo (JP); Kiichi Sato, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 65 days.

(21) Appl. No.: 14/425,196

(22) PCT Filed: Sep. 6, 2013

(86) PCT No.: PCT/JP2013/074076
§ 371 (c)(1),
(2) Date: Mar. 2, 2015

(87) PCT Pub. No.: WO2014/038663
PCT Pub. Date: Mar. 13, 2014

(65) Prior Publication Data
US 2015/0259299 A1 Sep. 17, 2015

(30) Foreign Application Priority Data

Sep. 7, 2012 (JP) .................................. 2012-197914

(51) Int. Cl.
| C07D 235/14 | (2006.01) |
| C07D 235/12 | (2006.01) |
| C07D 405/12 | (2006.01) |
| C07D 309/12 | (2006.01) |
| C07D 309/06 | (2006.01) |

(52) U.S. Cl.
CPC ........... *C07D 235/12* (2013.01); *C07D 235/14* (2013.01); *C07D 309/06* (2013.01); *C07D 309/12* (2013.01); *C07D 405/12* (2013.01); *C07B 2200/13* (2013.01)

(58) Field of Classification Search
CPC ............................ C07D 235/12; C07D 235/14
See application file for complete search history.

(56) References Cited

U.S. PATENT DOCUMENTS

2009/0018177 A1    1/2009  Hirano et al.
2009/0181964 A1*   7/2009  Hirano ................. C07D 235/12
                                               514/234.5

FOREIGN PATENT DOCUMENTS

| CN | 1964950 A | 5/2007 |
| CN | 101142193 A | 3/2008 |
| EP | 1 864 976 A1 | 12/2007 |
| WO | WO 2006/106812 A1 | 10/2006 |

OTHER PUBLICATIONS

Combined Chinese Office Action and Search Report issued Feb. 1, 2016 in Patent Application No. 201380046596.2 (with English language translation).
Guoyuan Lu, "Organic Reaction and Organic Synthesis" Science Press, Jun. 1, 2009, pp. 292 and 295 (with English language translation).
Bo Lu, et al., "Dihydropyran-Effective Hydroxyl-Protecting Reagent" Chemical Reagents, vol. 21, No. 2, Feb. 28, 1999, pp. 87-92.
International Search Report issued Oct. 1, 2013 in PCT/JP2013/074076.
International Preliminary Report on Patentability and Written Opinion issued Mar. 10, 2015 in PCT/JP2013/074076 (English Translation Only).
Makoto Ono et al., "Crystalline Morphology Screening of Drugs", Pharmacia, Nov. 1, 2011, vol. 47, No. 11, with English Translation, 20 pages.
Mitsuhisa Yamano et al., "Process Research on New Drugs and Crystal Polymorphs", Pharmacia, Apr. 1, 2009, vol. 45, No. 4, with English Translation, 18 pages.
Kazuhide Ashizawa et al., "Preformulation Studies on the Drug Discovery Stage", Pharm Stage, Sep. 15, 2009, vol. 9, No. 6, with English Translation, 22 pages.
Extended European Search Report issued Feb. 8, 2016 in Patent Application No. 13835562.3.

* cited by examiner

*Primary Examiner* — Laura L. Stockton
(74) *Attorney, Agent, or Firm* — Oblon, McClelland, Maier & Neustadt, L.L.P.

(57) ABSTRACT

Provided are a method for producing a sulfonyl amidine compound, which has an excellent gonadotropin releasing hormone receptor antagonism and is useful as a therapeutic agent for gonadotropin-dependent diseases (for example, prostate cancer, breast cancer, endometriosis, uterine fibroid, prostatic hyperplasia, or the like) or a salt thereof, and a synthesis intermediate useful in the production method. The production method of the present invention controls formation of a by-product which is hardly removed unless column purification is conducted and racemization of a target compound, thereby obtaining the target compound with a high purity, and therefore, the production method is suitable for industrial production.

7 Claims, 6 Drawing Sheets

METHOD FOR PRODUCING SULFONYL AMIDINE COMPOUND

TECHNICAL FIELD

The present invention relates to a method for producing (2R)—N-({5-[3-(2,5-difluorophenyl)-2-(1,3-dihydro-2H-benzoimidazol-2-ylidene)-3-oxopropanoyl]-2-fluorophenyl}sulfonyl)-2-hydroxypropanimidamide (hereinafter referred to as a "compound A" or "a compound of the formula (I)" in some cases), or a synthesis intermediate in the production method. The present invention further relates to a crystal of the compound of the formula (I).

BACKGROUND ART

It is known that the compound A has an excellent gonadotropin releasing hormone (GnRH) receptor antagonistic action and is useful as a therapeutic agent for gonadotropin-dependent diseases (for example, prostate cancer, breast cancer, endometriosis, uterine fibroid, prostatic hyperplasia, or the like) (Patent Document 1).

In Patent Document 1, the compound A is disclosed in Example 726 and it is described that the compound A is produced by the same method as the compound of Example 696. Here, it is described that the compound of Example 696 is produced by subjecting (2R)-2-hydroxypropanimidamide hydrochloride to a sulfonyl amidination reaction with 5-[2-(1,3-dihydro-2H-benzoimidazol-2-ylidene)-3-(3-fluorophenyl)-3-oxopropanoyl]-2-fluorobenzenesulfonyl chloride in the presence of sodium hydride, in tetrahydrofuran, followed by a liquid separation operation and purification with columns. However, this production method requires purification with columns so as to remove the impurities and thus, it has been desired to establish a production method for obtaining a compound A at a high purity, which is suitable for industrial production, without carrying out purification with columns.

RELATED ART

Patent Document

Patent Document 1: Pamphlet of WO 2006/106812

DISCLOSURE OF INVENTION

Problems to be Solved by the Invention

It is an object of the present invention to provide a production method for obtaining a compound A with a high purity, which is suitable for industrial production, without carrying out purification with columns.

Means for Solving the Problems

The present inventors have investigated a production method for obtaining a compound A with a high purity, which is suitable for industrial production, without carrying out purification with columns, and first, they have further conducted tests on the production method described in Patent Document 1 (sulfonyl amidination). As a result, it has been proven that in the production method, the compound A that is a target product is obtained with a purity of 80.27%, but a compound B shown below is contained as a by-product in the amount of 7.49%, which is hardly removed if the purification is not carried out with columns and, further, the compound A is slightly racemized (for details, refer to Comparative Example as described later).

[Chem. 1]

Compound B

Accordingly, as a result of investigation of an approach to control the by-product of the compound B, it has been conceived to provide a step of protecting-deprotecting a hydroxyl group of (2R)-2-hydroxypropanimidamide hydrochloride in the sulfonyl amidination, and various protective groups have been investigated. As a result, it has been unexpectedly found that in the case of employing a 2-tetrahydropyranyl group as the protective group, a by-product of the compound B which is hardly removed without purification with columns is controlled, and further, racemization of the compound A is also remarkably controlled. Based on these findings, a production method for obtaining a compound A with a high purity, which is suitable for industrial production, without carrying out purification with columns, is established, thereby completing the present invention.

That is, the present invention relates to the following.

[1] A method for producing a compound of the formula (I) or a salt thereof through deprotection of a 2-tetrahydropyranyl group from a compound (4) or a salt thereof:

[Chem. 2]

(in the formula, Me means a methyl group and THP means a 2-tetrahydropyranyl group).

[2] A method for producing the compound (4) or a salt thereof described in [1], in which a compound (2) is subjected to sulfonyl amidination with a compound (3):

[Chem. 3]

(in the formula, Me means a methyl group, THP means a 2-tetrahydropyranyl group, and HCl means that the compound is a hydrochloride salt).

[3] The method as described in [1], in which the compound (4) or a salt thereof is a compound (4) or a salt thereof produced by the method as described in [2].

[4] The method as described in [3], in which a compound (2) produced by 2-tetrahydropyranylation of the compound (1) is used:

[Chem. 4]

[5] (2R)-2-(Tetrahydro-2H-pyran-2-yloxy)propanimidamide or a salt thereof.

[6] (2R)—N-({5-[3-(2,5-Difluorophenyl)-2-(1,3-dihydro-2H-benzoimidazol-2-ylidene)-3-oxopropanoyl]-2-fluorophenyl}sulfonyl)-2-(tetrahydro-2H-pyran-2-yloxy)propanimidamide or a salt thereof.

[7] A crystal of the compound of the formula (I), which has peaks at 2θ)(°)=about 5.7, about 11.4, about 13.0, about 16.1, and about 18.5 in the powder X-ray diffraction using Cu as a radiation source.

[8] A crystal of the compound of the formula (I), which has peaks at 2θ)(°)=about 9.3, about 11.6, about 20.6, about 23.4, and about 29.4 in the powder X-ray diffraction using Cu as a radiation source.

Effects of the Invention

According to the present invention, a production method for obtaining a compound A or a salt thereof with a high purity, which is suitable for industrial production, and a synthesis intermediate in the production method are provided. Further, a crystal of the compound A is provided.

EMBODIMENTS FOR CARRYING OUT THE INVENTION

Hereinafter, the present invention will be described in detail.

(Production Method)

The production methods (Steps 1 to 3) for the compound of the formula (I) (compound A) or a salt thereof of the present invention are shown in the schemes below and embodiments of the respective steps will be described. Further, in the schemes below, Me means a methyl group, THP means a 2-tetrahydropyranyl group, and HCl means that the compound is a hydrochloride salt.

[Chem. 5]

(Step 1)

The present step is a step of obtaining (2R)-2-(tetrahydro-2H-pyran-2-yloxy)propanimidamide hydrochloride (2) by 2-tetrahydropyranylation of a hydroxyl group of (2R)-2-hydroxypropanimidamide hydrochloride (1). In this reaction, the compound (1) and 3,4-dihydro-2H-pyran (DHP) are used in equivalent amounts, or either thereof in an excess amount, and a mixture thereof is stirred in a solvent which is inert to the reaction, in a range from cooling to heating, preferably from ice-cooling to 40° C., in the presence of a catalytic amount of an acid, usually for 1 hour to 2 days. Examples of the solvent used herein are not particularly limited as long as the compound (1) is dissolved therein, but in one embodiment, examples of the solvent include N,N-dimethylformamide (DMF), N,N-dimethylacetamide, 1,3-dimethyl-2-imidazolidinone (DMI), and N-methyl-2-pyrrolidone (NMP). Examples of the acid are not particularly limited, but in one embodiment, include p-toluenesulfonic acid monohydrate, pyridinium p-toluenesulfonate, and methanesulfonic acid. Further, the compound (2) may be isolated and then used in the next reaction, or may be used to perform the next reaction without being isolated.

(Step 2)

The present step is a step of obtaining (2R)—N-({5-[3-(2,5-difluorophenyl)-2-(1,3-dihydro-2H-benzoimidazol-2-ylidene)-3-oxopropanoyl]-2-fluorophenyl}sulfonyl)-2-(tetrahydro-2H-pyran-2-yloxy)propanimidamide (4) by reacting (2R)-2-(tetrahydro-2H-pyran-2-yloxy)propanimidamide hydrochloride (2) obtained in Step 1 with 5-[3-(2,5-difluorophenyl)-2-(1,3-dihydro-2H-benzoimidazol-2-ylidene)-3-oxopropanoyl]-2-fluorobenzenesulfonyl chloride (3). In this reaction, the compound (2) and the compound (3) are used in equivalent amounts, or either thereof in an excess amount, and a mixture thereof is stirred in a solvent which is inert to the reaction, in a range from cooling to heating, preferably from ice-cooling to 40° C., in the presence of a base, usually for 1 hour to 2 days. Examples of the solvent used herein are not particularly limited, but in one embodiment, examples of the solvent include DMF, DMI, NMP, tetrahydrofuran (THF), isopropyl acetate (AcOiPr), ethyl acetate (AcOEt), dimethoxyethane, acetonitrile (MeCN), acetone, toluene, and a mixed solvent thereof. It may sometimes be advantageous to carry out a bi-phase reaction by further adding water to the mixture. Examples of the base include organic bases such as triethylamine, diisopropylethylamine, N-methylmorpholine and the like, or inorganic bases such as potassium carbonate, sodium carbonate, sodium hydrogen carbonate, cesium carbonate and the like, but in one embodiment, triethylamine. Further, the compound (4) may be isolated and then used in the next reaction, or may be used to perform the next reaction without being isolated.

(Step 3)

The present step is a step of obtaining the compound of the formula (I) (compound A) or a salt thereof by deprotecting (2R)—N-({5-[3-(2,5-difluorophenyl)-2-(1,3-dihydro-2H-benzoimidazol-2-ylidene)-3-oxopropanoyl]-2-fluorophenyl}sulfonyl)-2-(tetrahydro-2H-pyran-2-yloxy)propanimidamide (4) obtained in Step 2. In this reaction, the compound (4) is dissolved in a suitable solvent, followed by addition of an acid and stirring in a range from cooling to heating, preferably from ice-cooling to 40° C., usually for 1 hour to 2 days. Examples of the solvent used herein are not particularly limited, but in one embodiment, examples of the solvent include esters such as AcOEt, AcOiPr and the like; alcohols such as methanol (MeOH), ethanol (EtOH), isopropanol (IPA) and the like; ethers such as THF, dioxane and the like; or a mixed solvent thereof, and it may sometimes be advantageous to carry out a reaction by further adding water to the mixture. Examples of the acid include pyridinium p-toluenesulfonate, hydrogen chloride, hydrochloric acid, formic acid, and acetic acid, and the acetic acid can be used as a solvent as well as an acid in the present step. Further, the compound of the formula (I) (compound A) or a salt thereof can also be prepared by subjecting a free form of the compound of the formula (I) to a conventional salt forming reaction.

In the present specification, the term "about" included in the description of an endothermal peak (° C.) in the differential scanning calorimetry (DSC analysis) and a diffraction angle (2θ(°)) in the powder X-ray diffraction spectrum is meant to include a usually acceptable error range in the data measurement method, and typically means a value of the endothermal peak and the diffraction angle. The error range is, in one embodiment, ±2° C. in the DSC analysis, and is, in one embodiment, ±0.2° C. in the powder X-ray diffraction.

Furthermore, with the powder X-ray diffraction spectrum, crystal lattice intervals and the overall patterns are important for identification of crystals in terms of the properties of the data, and since the relative intensity may vary slightly depending on the direction of crystal growth, the particle size, and the measurement conditions, it should not be strictly construed.

The compound disclosed in the specification may be a free form or may form a salt unless otherwise specified, and in one embodiment of a salt of the compound, and specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyl tartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum, or organic bases such as methylamine, ethylamine, ethanolamine, lysine, and ornithine, salts with various amino acids or amino acid derivatives such as acetylleucine, ammonium salts, and the like.

Moreover, the compound disclosed in the present specification may be any of various hydrates or solvates of a free form or a salt thereof unless otherwise specified, and for the synthesis intermediate, a production method using the same is also included in the present invention. Further, the compound disclosed in the present specification may be any compound labeled with various radioactive or non-radioactive isotopes, and for the synthesis intermediate, a production method using the same is also included in the present invention.

Further, the compounds disclosed in the present specification may exist in the form of tautomers or geometrical isomers in some cases. In the present specification, the compounds having the tautomers or geometrical isomers shall be described in only one form of isomer, yet the present invention may also include other tautomers or geometrical isomers thereof, isolated forms of the tautomers or geometrical isomers, or a mixture thereof.

In addition, the compounds disclosed in the present specification may have asymmetric carbon atoms or axial asymmetry in some cases, and correspondingly, they may exist in the form of steromers based on the asymmetric carbon atoms or axial asymmetry. In the present specification, for example, there are compounds that exist in the form of steromers based on the asymmetric carbon atom at the second position of a 2-tetrahydropyranyl group, and the present invention includes both an isolated form of the steromers of the compounds or a mixture thereof.

The compounds disclosed in the present specification are isolated and purified as a free compound, a salt, a hydrate, or a solvate thereof. Salt of the compounds disclosed in the present specification may also be prepared by subjecting a free form to a conventional salt forming reaction.

Isolation and purification are carried out by employing ordinary chemical operations such as extraction, fractional crystallization, various types of fractional chromatography, and the like.

EXAMPLES

Hereinafter, the present invention will be described in more detail with reference to Examples, but the present invention is not limited to Examples. Further, a production method for 5-[3-(2,5-difluorophenyl)-2-(1,3-dihydro-2H-benzoimidazol-2-ylidene)-3-oxopropanoyl]-2-fluorobenzenesulfonyl chloride (3) which is a starting compound will be shown as Preparation Examples. Further, the test results obtained from a production method for the compound of the formula (I) (compound A) described in Patent Document 1, and the results obtained when a protective group other than the 2-tetrahydropyranyl group of the present invention is used as a protective group for the hydroxyl group of (2R)-2-hydroxypropanimidamide hydrochloride (1) are shown as Comparative Examples.

Further, the measurement using differential scanning calorimetry analysis (DSC analysis) and powder X-ray diffraction spectrum are carried out in the following manner.

<Differential Scanning Calorimetry Analysis (DSC Analysis)>

The differential scanning calorimetry analysis was measured using DSC7020 (SII) under the conditions of 30° C. to 500° C. (10° C./min), $N_2$ (40 mL/min), and using a stainless steel sample pan with a seal.

<Powder X-Ray Diffraction>

The powder X-ray diffraction was measured using Miniflex under the conditions of a tube of Cu, a tube current of 15 mA, a tube voltage of 30 kV, a sampling width of 0.010°, a scanning speed of 2.0°/min, a wavelength of 1.541841 angstroms, and a measurement diffraction angle (2θ) of 3° to 35°.

In addition, the purity of the compound was confirmed using high performance liquid chromatography (HPLC).

Furthermore, for the sake of convenience, a concentration mol/l is expressed as M. For example, a 2 M aqueous hydrogen chloride solution means a 2 mol/l aqueous hydrogen chloride/IPA solution.

Example 1

Production of Compound (2)

Under a nitrogen atmosphere, to a solution of 3.0 g of (2R)-2-hydroxypropanimidamide hydrochloride (1) in NMP (21.6 mL) were added 8.31 g of 3,4-dihydro-2H-pyran and 139 mg of methanesulfonic acid at an inner temperature of 20° C. to 30° C., followed by stirring at the same temperature for 22 hours. To the reaction mixture was added 90 mL of diisopropyl ether, followed by stirring for 1 hour and 40 minutes. The precipitated crystal was collected by filtration and washed with 30 mL of AcOiPr. To the obtained crystal was added 90 mL of AcOiPr, followed by stirring at room temperature for 30 minutes. The mixture was filtered, washed with 30 mL of AcOiPr, and then dried at 40° C.

overnight under reduced pressure to obtain 4.89 g of (2R)-2-(tetrahydro-2H-pyran-2-yloxy)propanimidamide hydrochloride (2) as a crystal.

The physicochemical data of the compound (2) are shown below.

$^1$H-NMR (DMSO-d6, 400 MHz): δ (ppm)=1.33-1.82 (6H, m), 1.38 (1.2H, d, J=6.8 Hz), 1.42 (1.8H, d, J=6.8 Hz), 3.42-3.52 (1H, m), 3.69-3.78 (1H, m), 4.44 (0.4H, q, J=6.8 Hz), 4.53-4.55 (0.6H, br), 4.58 (0.6H, q, J=6.8 Hz), 4.73 (0.4H, dd, J=2.4, 4.8 Hz), 8.98-9.14 (3H, m)

ESI-MS: m/z=173 ([M+H]$^+$)

Example 2

Production of Compound (4)

Under a nitrogen atmosphere, to a solution of 1.39 g of (2R)-2-hydroxypropanimidamide hydrochloride (1) in DMI (10 mL) were added 3.41 g of 3,4-dihydro-2H-pyran and 58.5 mg of methanesulfonic acid at an inner temperature of 20° C. to 30° C., followed by stirring at the same temperature for 40 hours. To the reaction mixture were added 25 mL of AcOiPr and 3.39 g of triethylamine at an inner temperature of 20° C. to 30° C., followed by stirring at the same temperature for 15 minutes. Then, 5.0 g of 5-[3-(2,5-difluorophenyl)-2-(1,3-dihydro-2H-benzoimidazol-2-ylidene)-3-oxopropanoyl]-2-fluorobenzenesulfonyl chloride (3) was added thereto at an inner temperature of 24° C. to 33° C., followed by stirring at the same temperature for 1 hour. To the reaction mixture was added 20 mL of water at an inner temperature of 20° C. to 30° C., and the organic layer was washed with 18.5 mL of a 5% aqueous sodium hydrogen carbonate solution twice and 15 mL of a 20% aqueous sodium chloride solution once. The organic layer was concentrated under reduced pressure (at an outer temperature of 30° C. to 40° C.), and the HPLC analysis results of the obtained residue are shown below.

<HPLC Analysis Conditions>

Column: YMC-Pack ODS-A, AA12S05-1546WT (manufactured by YMC Co., Ltd.)

Particle diameter of 5 μm, inner diameter of 4.6 mm, length of 150 mm

Column temperature: a constant temperature of around 30° C.

Mobile phase: 0.01 M aqueous potassium hydrogen diphosphate solution/MeCN=4/6

Flow rate: 1.0 mL/min

Measurement wavelength: 235 nm

<HPLC Analysis Results>

Under the conditions above, a peak having a retention time of about 5.4 minutes and a peak having a retention time of about 5.7 minutes were found, and the HPLC area percentages were 48.23% and 40.62%, respectively.

Furthermore, a part of the obtained residue was purified by silica gel chromatography (eluent: AcOEt/heptane) and in the HPLC analysis above, the peak having a retention time of about 5.4 minutes and the peak having a retention time of about 5.7 minutes were isolated together to obtain (2R)—N-({5-[3-(2,5-difluorophenyl)-2-(1,3-dihydro-2H-benzoimidazol-2-ylidene)-3-oxopropanoyl]-2-fluorophenyl}sulfonyl)-2-(tetrahydro-2H-pyran-2-yloxy)propanimidamide (4) as an amorphous material.

The physicochemical data of the compound (4) are shown below.

$^1$H-NMR (DMSO-d6, 400 MHz): δ (ppm)=1.20 (1.2H, d, J=6.8 Hz), 1.25 (1.8H, d, J=6.8 Hz), 1.30-1.78 (6H, m), 3.25-3.40 (1H, m), 3.58-3.72 (1H, m), 4.15 (0.4H, q, J=6.8 Hz), 4.28 (0.6H, q, J=6.8 Hz), 4.40 (0.6H, br), 4.63 (0.4H, br), 6.70-6.80 (1H, m), 6.88-6.97 (1H, m), 6.97-7.04 (1H, m), 7.06-7.14 (1H, m), 7.25-7.33 (2H, m), 7.50-7.60 (1H, m), 7.68-7.78 (3H, m), 8.14 (0.4H, s), 8.17 (0.6H, s), 8.24 (0.4H, s), 8.50 (0.6H, s), 13.18 (2H, s)

ESI-MS: m/z=629 ([M+H]$^+$)

From the physicochemical data above, it was believed that in the HPLC analysis above, a peak having a retention time of about 5.4 minutes and a peak having a retention time of about 5.7 minutes correspond to two kinds of diastereomers based on the asymmetric carbon at the 2 position of the tetrahydropyran ring of the compound (4), respectively.

Example 3

Production of X Type Crystal of Compound A

Under a nitrogen atmosphere, to a solution of 1.67 g of (2R)-2-hydroxypropanimidamide hydrochloride (1) in NMP (12 mL) were added 4.61 g of 3,4-dihydro-2H-pyran and 70.2 mg of methanesulfonic acid at an inner temperature of 20° C. to 30° C., followed by stirring at the same temperature for 15 hours. To the reaction mixture were added 36 mL of THF and 4.07 g of triethylamine at an inner temperature of 15° C. to 30° C., followed by stirring at the same temperature for 15 minutes. Then, 6.0 g of 5-[3-(2,5-difluorophenyl)-2-(1,3-dihydro-2H-benzoimidazol-2-ylidene)-3-oxopropanoyl]-2-fluorobenzenesulfonyl chloride (3) was added thereto at an inner temperature of 15° C. to 30° C., followed by stirring at an inner temperature of 20° C. to 30° C. for 30 minutes. To the reaction mixture were added 36 mL of AcOEt and 24 mL of water, followed by carrying out liquid separation at an inner temperature of 20° C. to 30° C., and the organic layer was washed with 24 mL of a 5% aqueous sodium hydrogen carbonate solution twice and 18 mL of a 20% aqueous sodium chloride solution once. The obtained organic layer was concentrated to about 18 mL under reduced pressure, and then 60 mL of AcOEt was added thereto, followed by concentrating to about 18 mL under reduced pressure (at an outer temperature of 30° C. to 40° C.). 6 mL of AcOEt and 60 mL of IPA were added thereto, followed by dropwise addition of 1.2 mL of a 2 M hydrogen chloride/IPA solution at an inner temperature of 20° C. to 30° C., stirring at the same temperature for 6 hours, and then cooling to an inner temperature of 0° C. to 10° C. The reaction solution was added dropwise to a mixed liquid of 48 mL of AcOEt and 60 mL of a 2.5% aqueous sodium hydrogen carbonate solution at an inner temperature of 0° C. to 10° C., followed by washing with 12 mL of AcOEt. The organic layer was collected by filtration, and washed sequentially with 30 mL of a 5% aqueous sodium hydrogen carbonate solution and 30 mL of a 20% aqueous sodium chloride solution (at an inner temperature of 20° C. to 30° C.). The organic layer was concentrated to about 24 mL under reduced pressure and then 60 mL of EtOH was added thereto. The mixture was concentrated to about 24 mL under reduced pressure and 30 mL of EtOH was further added thereto, followed by concentrating to about 24 mL under reduced pressure (at an outer temperature of 30° C. to 40° C.). 18 mL of EtOH and 12 mL of water were added to the mixture at an inner temperature of 40° C. or lower to afford a homogeneous solution, and 15 mL of water was added dropwise thereto at an inner temperature of 20° C. to 30° C. for 1 hour, followed by stirring for 1 hour. Thereafter, the mixture was cooled to an inner temperature of 0° C. to 10° C. for 1 hour and stirred at the same temperature for 12 hours, and the precipitated crystal was collected by filtration, washed with 12 mL of a EtOH/water mixed solution (1/1 (v/v)), and dried at 60° C. overnight under reduced pressure to obtain 5.93 g of the compound A as a crystal.

Here, the physicochemical data of the crystal of the obtained compound A are shown below.

$^1$H-NMR (DMSO-d6, 400 MHz): δ (ppm)=1.07 (0.9H, t, J=7.2 Hz), 1.23 (3H, d, J=6.8 Hz), 3.45 (0.6H, dq, J=5.2 Hz, 7.2 Hz), 4.16 (1H, dq, J=4.8 Hz, 6.8 Hz), 4.36 (0.3H, t, J=5.2 Hz), 5.94 (1H, d, J=4.8 Hz), 6.77-6.83 (1H, m), 6.95-7.02 (1H, m), 7.04-7.09 (1H, m), 7.12-7.17 (1H, m), 7.32-7.37 (2H, m), 7.59-7.63 (1H, m), 7.76-7.81 (3H, m), 8.19 (1H, brs), 8.32 (1H, brs), 13.23 (2H, s)

ESI-MS: m/z=545 ([M+H]$^+$)

Figure 1:
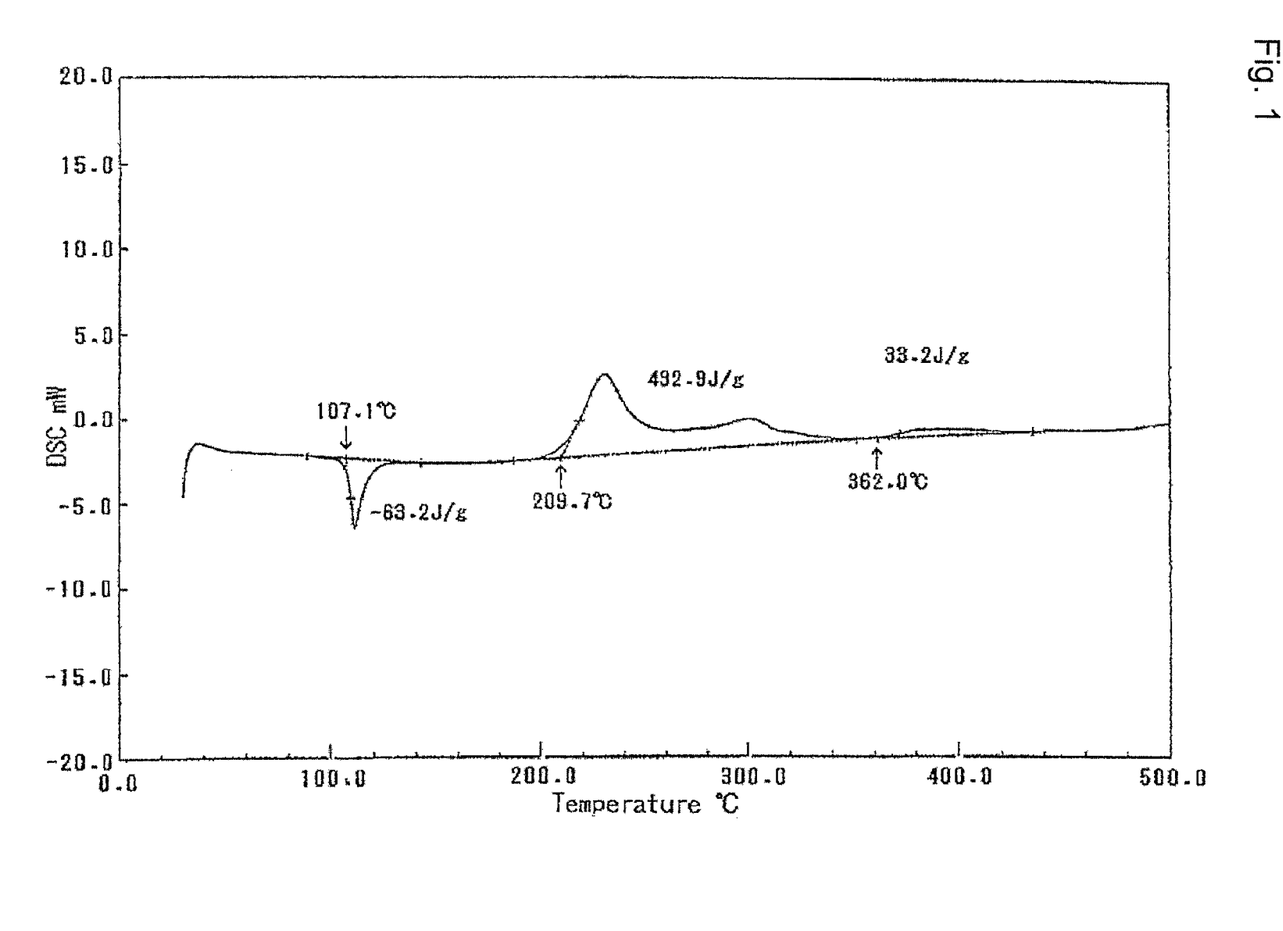
FIG. 1 is a chart showing the results of differential scanning calorimetry (DSC analysis) of a crystal (X type crystal) of the compound A obtained in Example 3.
Figure 2:
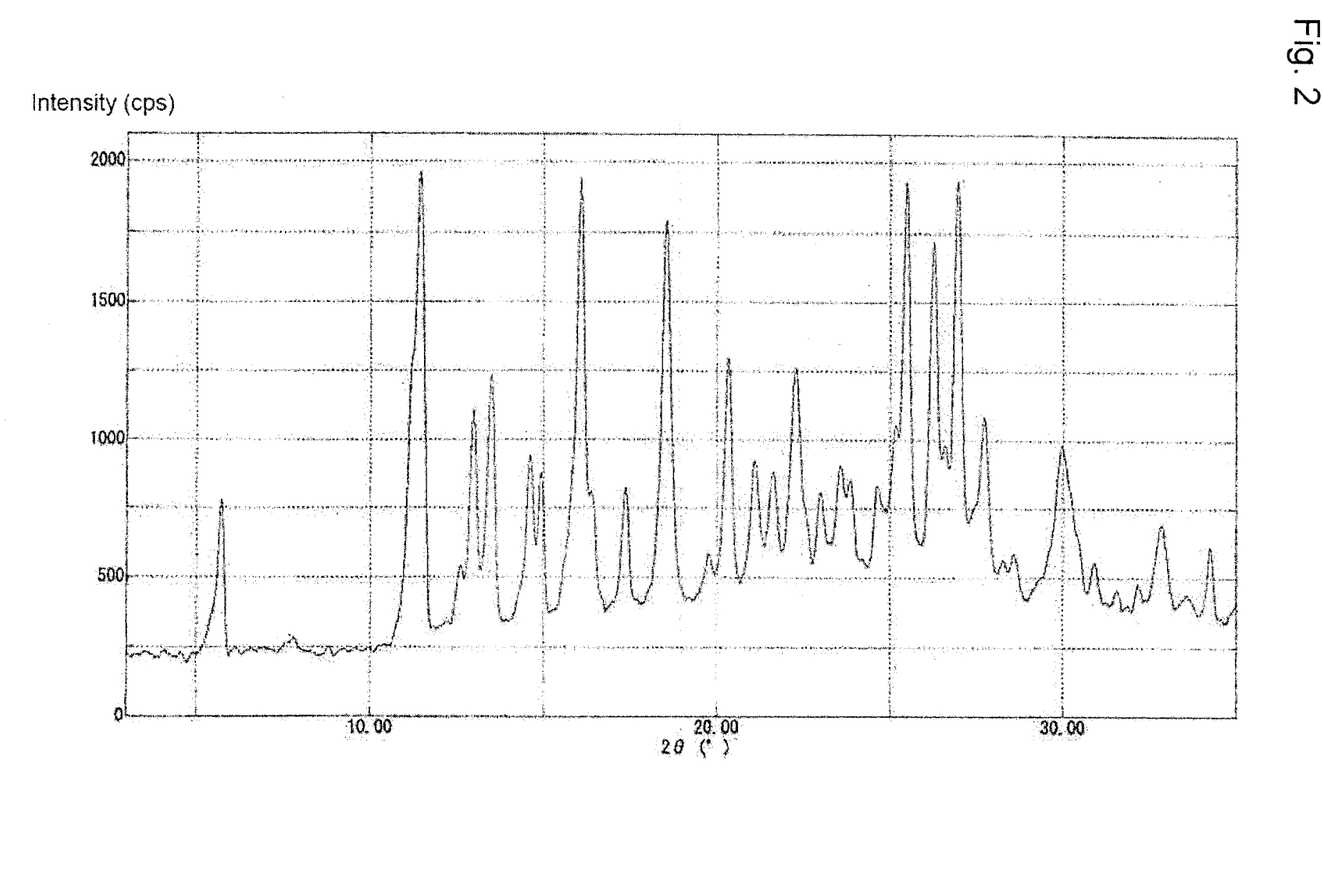
FIG. 2 is a chart of a powder X-ray diffraction spectrum of a crystal (X type crystal) of the compound A obtained in Example 3, in which the vertical axis represents the intensity and the horizontal axis represents a diffraction angle (2θ(°)).

From the $^1$H-NMR data above, it was thus demonstrated that the crystal of the obtained compound A contains EtOH at a molar ratio of 3/10. The chart showing the results of the differential scanning calorimetry analysis (DSC analysis) and the chart of the powder X-ray diffraction spectrum of this crystal are shown in FIGS. 1 and 2, respectively.

The crystal (X type crystal) of the compound A is a crystal which has peaks at 2θ (°)=around 5.7, about 11.4, about 13.0, about 16.1, and about 18.5 in the powder X-ray diffraction using Cu as a radiation source. Further, this crystal (X type crystal) of the compound A absorbed heat at around 107° C. in the differential scanning calorimetry analysis (DSC analysis).

Furthermore, the HPLC analysis results of the reaction mixture before crystallization of the compound A and/or the X type crystal of the compound A obtained after crystallization are shown in Tables 1 and 2, respectively.

TABLE 1

Chemical Purity

| | Reaction mixture before crystallization | X type crystal of the compound A obtained after crystallization |
|---|---|---|
| Compound A (retention time: about 11.1 minutes) | 93.72% | 97.76% |
| One diastereomer of compound (4) (retention time: about 21.6 minutes) | 0.33% | 0.26% |
| The other diastereomer of compound (4) (retention time: about 22.1 minutes) | 0.23% | 0.21% |
| Compound B (retention time: about 27.8 minutes) | 0.31% | 0.32% |

The numbers in the Table represent HPLC area percentages (%).

<HPLC Analysis Conditions>

Column: YMC-Pack ODS-A, AA12S05-1546WT (manufactured by YMC Co., Ltd.)

Particle diameter of 5 μm, inner diameter of 4.6 mm, length of 150 mm

Column temperature: a constant temperature of around 30° C.

Mobile phase:

Liquid A: 0.01 M aqueous potassium dihydrogen phosphate solution

Liquid B: MeCN

Gradient conditions:

0 min to 10 min: A/B=63/37

10 min to 20 min: A/B=63/37→A/B=40/60

20 min to 40 min: A/B=40/60

Flow rate: 1.0 mL/min

Measurement wavelength: 235 nm

From Table 1, it was confirmed that in the present production process, the by-production of the compound B can be controlled to about 1/300 or less relative to the compound A.

TABLE 2

Optical Purity

| | X type crystal of the compound A obtained after crystallization |
|---|---|
| Compound A (retention time: about 27.1 minutes) | 98.56% |
| Enantiomer of compound A (retention time: about 19.1 minutes) | 0.07% |

The numbers in the Table represent HPLC area percentages (%).

<HPLC Analysis Conditions>

Column: CHIRALCEL OJ-RH (manufactured by Daicel Chemical Industries, Ltd.)

Particle diameter of 5 μm, inner diameter of 4.6 mm, length of 150 mm

Column temperature: a constant temperature of around 40° C.

Mobile phase: MeCN/water=3/7

Flow rate: about 0.5 mL/min

Measurement wavelength: 322 nm

From Table 2, it was confirmed that the racemization rate of the compound A is about 0.07%.

Example 4

Production-1 of Y Type Crystal of Compound A: Examples not Using Seed Crystal

Under a nitrogen atmosphere, to a solution of 1.0 g of the X type crystal of the compound A in acetone (5 mL) was added dropwise 3.3 mL of heptane at an inner temperature of 45° C. to 55° C., followed by stirring at the same temperature for 4 hours. Further, 4.7 mL of heptane was added dropwise thereto at the same temperature for 1 hour, followed by cooling to an inner temperature of 20° C. to 30° C. and stirring at the same temperature for 16 hours. The precipitated crystal was collected by filtration and washed with 2.6 mL of an acetone/heptane mixed solution (1/1.6 (v/v)) and dried overnight at 60° C. under reduced pressure to obtain 0.89 g of the compound A as a crystal.

Figure 4:
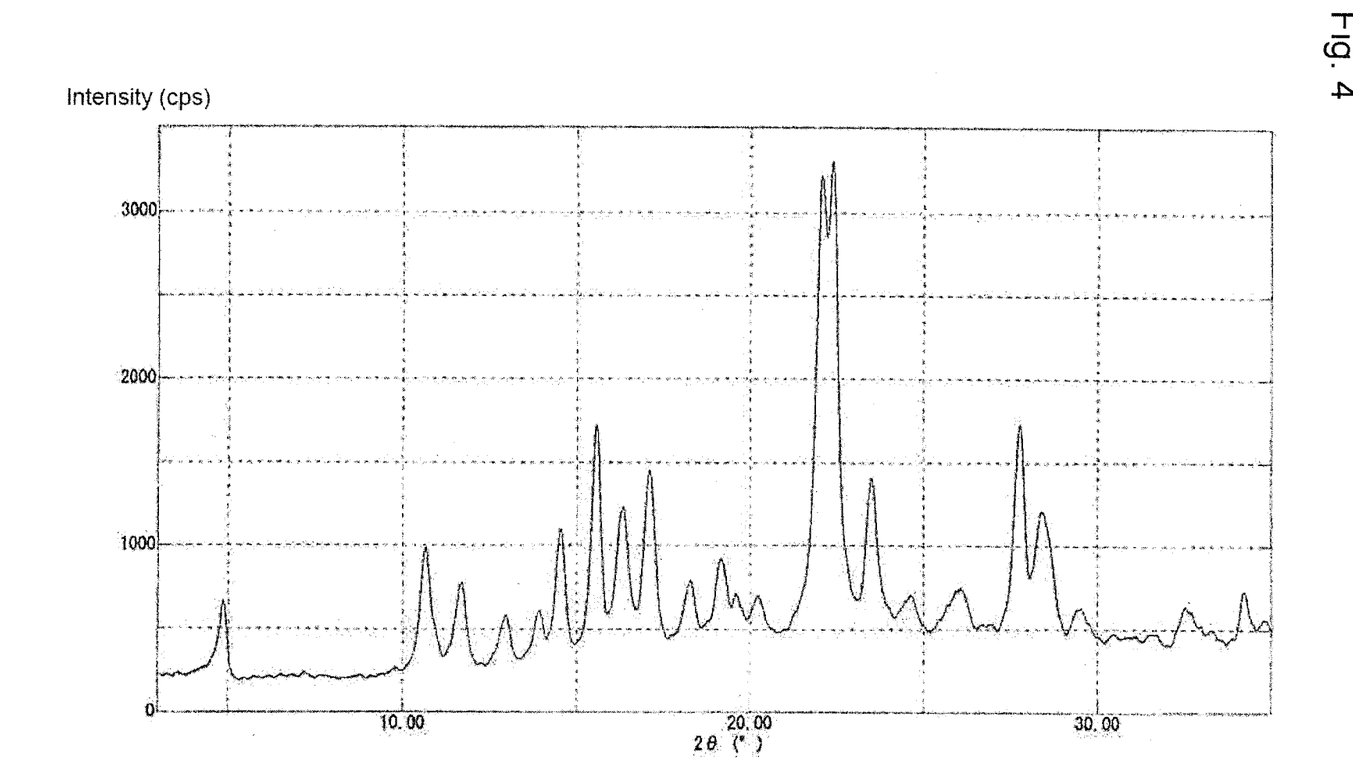
FIG. 4 is a chart of a powder X-ray diffraction spectrum of a crystal (Y type crystal) of the compound A obtained in Example 5, in which the vertical axis represents the intensity and the horizontal axis represents a diffraction angle (2θ(°)).

It was confirmed that the crystal of the compound A thus obtained is the same crystal as the crystal of the compound A obtained in Example 5 as described later from a chart of the powder X-ray diffraction spectrum.

Example 5

Production-2 of Y Type Crystal of Compound A: Examples Using Seed Crystal

Under a nitrogen atmosphere, a solution of 5.0 g of the X type crystal of the compound A in acetone (17.5 mL) was clarifying-filtered at an inner temperature of 20° C. to 40° C. and then washed with 7.5 mL of acetone. To the obtained filtrate was added dropwise 16.5 mL of heptane at an inner temperature of 45° C. to 55° C. for 10 minutes and then 10 mg of a Y type crystal of the compound A as a seed crystal was added thereto, followed by stirring at the same temperature for 2 hours. Subsequently, 23.5 mL of heptane was added dropwise thereto 1 hour, followed by stirring at the same temperature for 1 hour, and then cooling to an inner temperature of 20° C. to 30° C., and stirring at the same temperature for 12 hours. The precipitated crystal was collected by filtration and washed with 13 mL of an acetone/heptane mixed solution (5/8 (v/v)), washed, and then dried at 60° C. overnight under reduced pressure to obtain 4.42 g of the compound A as a crystal.

Here, the physicochemical data of the crystal of the obtained compound A are shown below.

$^1$H-NMR (DMSO-d6, 400 MHz): δ (ppm)=1.22 (3H, d, J=6.8 Hz), 4.15 (1H, dq, J=4.8 Hz, 6.8 Hz), 5.93 (1H, d, J=4.8 Hz), 6.76-6.83 (1H, m), 6.94-7.01 (1H, m), 7.03-7.08 (1H, m), 7.11-7.16 (1H, m), 7.31-7.37 (2H, m), 7.58-7.63 (1H, m), 7.75-7.81 (3H, m), 8.18 (1H, brs), 8.38 (1H, brs), 13.23 (2H, s)

ESI-MS: m/z=545 ([M+H]$^+$)

Figure 3:
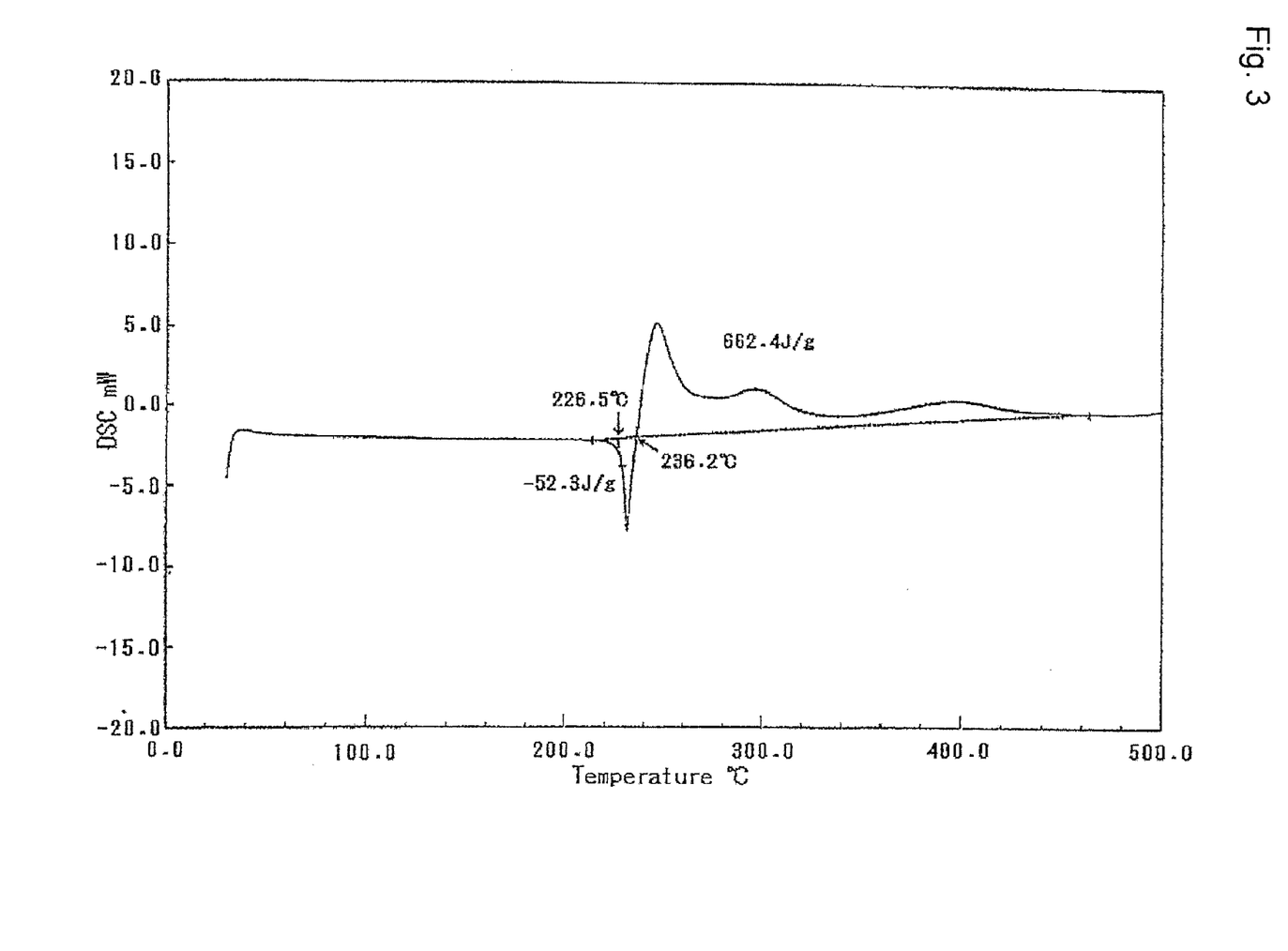
FIG. 3 is a chart showing the results of differential scanning calorimetry (DSC analysis) of a crystal (Y type crystal) of the compound A obtained in Example 5.

Furthermore, the chart showing the results of the differential scanning calorimetry analysis (DSC analysis) and the chart of the powder X-ray diffraction spectrum of this crystal are shown in FIGS. 3 and 4, respectively.

The crystal (Y type crystal) of the compound A is a crystal which has peaks at 2θ (°)=around 4.8, around 10.7, around 14.5, around 16.3, and around 22.0 in the powder X-ray diffraction using Cu as a radiation source. Further, this crystal (Y type crystal) of the compound A absorbed heat at around 227° C. in the differential scanning calorimetry analysis (DSC analysis).

Example 6

Production-1 of Z Type Crystal of Compound A

Under a nitrogen atmosphere, 1.0 g of the Y type crystal of the compound A was dissolved in 14 mL of EtOH and 2 mL of water, and 1 mg of the X type crystal of the compound A as a seed crystal was added thereto at an inner temperature of 40° C. to 50° C., followed by stirring at the same temperature for 1 hour. Subsequently, 7 mL of water was added dropwise thereto for 30 minutes, followed by further stirring at the same temperature for 1 hour, then cooling to an inner temperature of 0° C. to 10° C., and stirring at the same temperature overnight. The precipitated crystal was collected by filtration, washed with 5 mL of an EtOH/water mixed solution (1/1 (v/v)), and dried at 60° C. overnight under reduced pressure to obtain 1.06 g of the compound A as a crystal.

Here, the physicochemical data of the crystal of the obtained compound A are shown below.

$^1$H-NMR (DMSO-d6, 400 MHz): δ (ppm)=1.06 (2.4H, t, J=7.2 Hz), 1.23 (3H, d, J=7.2 Hz), 3.45 (1.6H, dq, J=5.2 Hz, 7.2 Hz), 4.16 (1H, dq, J=4.4 Hz, 7.2 Hz), 4.36 (0.8H, t, J=5.2 Hz), 5.93 (1H, d, J=4.4 Hz), 6.76-6.83 (1H, m), 6.94-7.01 (1H, m), 7.03-7.08 (1H, m), 7.11-7.16 (1H, m), 7.31-7.37 (2H, m), 7.58-7.63 (1H, m), 7.75-7.81 (3H, m), 8.19 (1H, brs), 8.32 (1H, brs), 13.23 (2H, s)

ESI-MS: m/z=545 ([M+H]$^+$)

Figure 5:
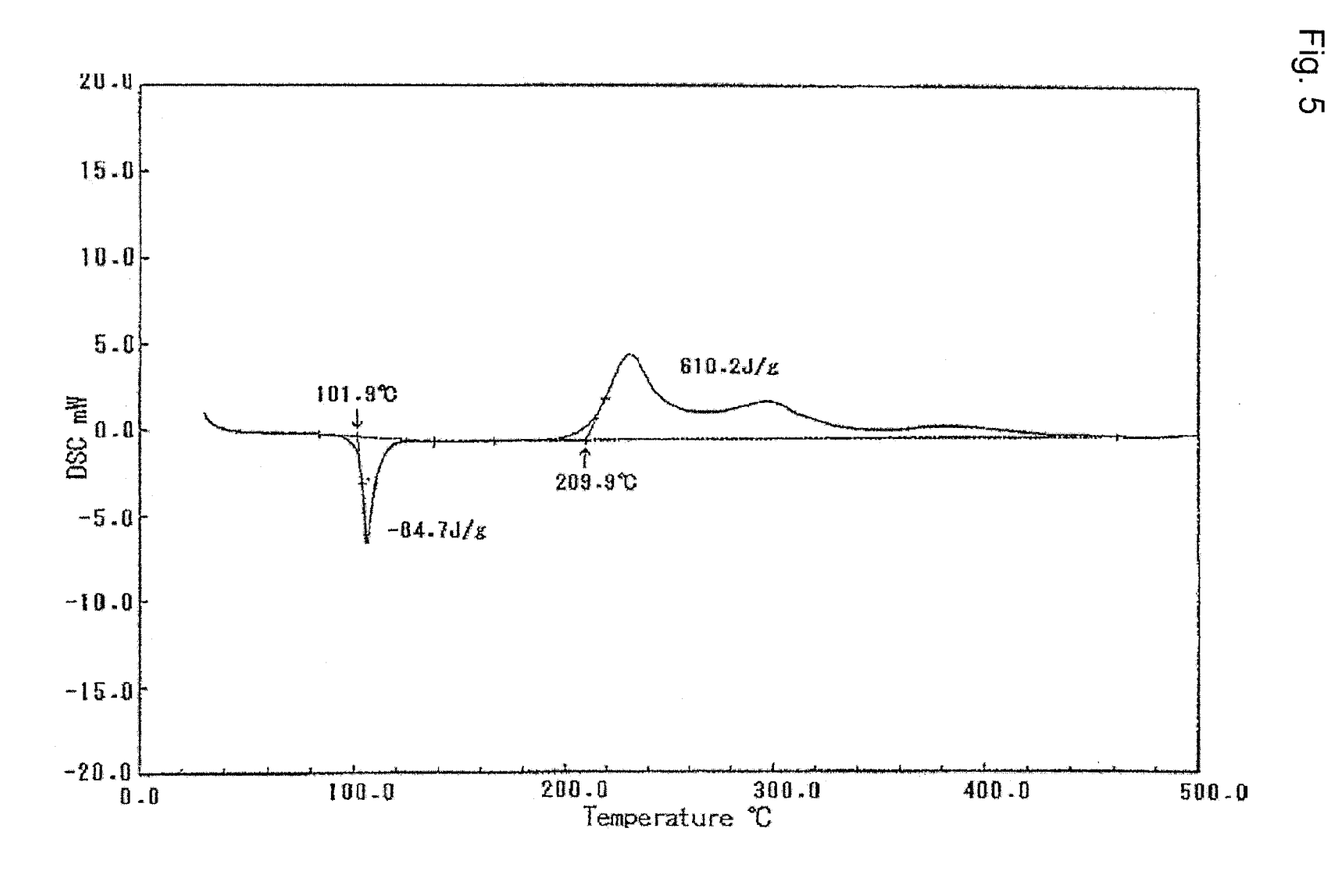
FIG. 5 is a chart showing the results of differential scanning calorimetry (DSC analysis) of a crystal (Z type crystal) of the compound A obtained in Example 6.
Figure 6:
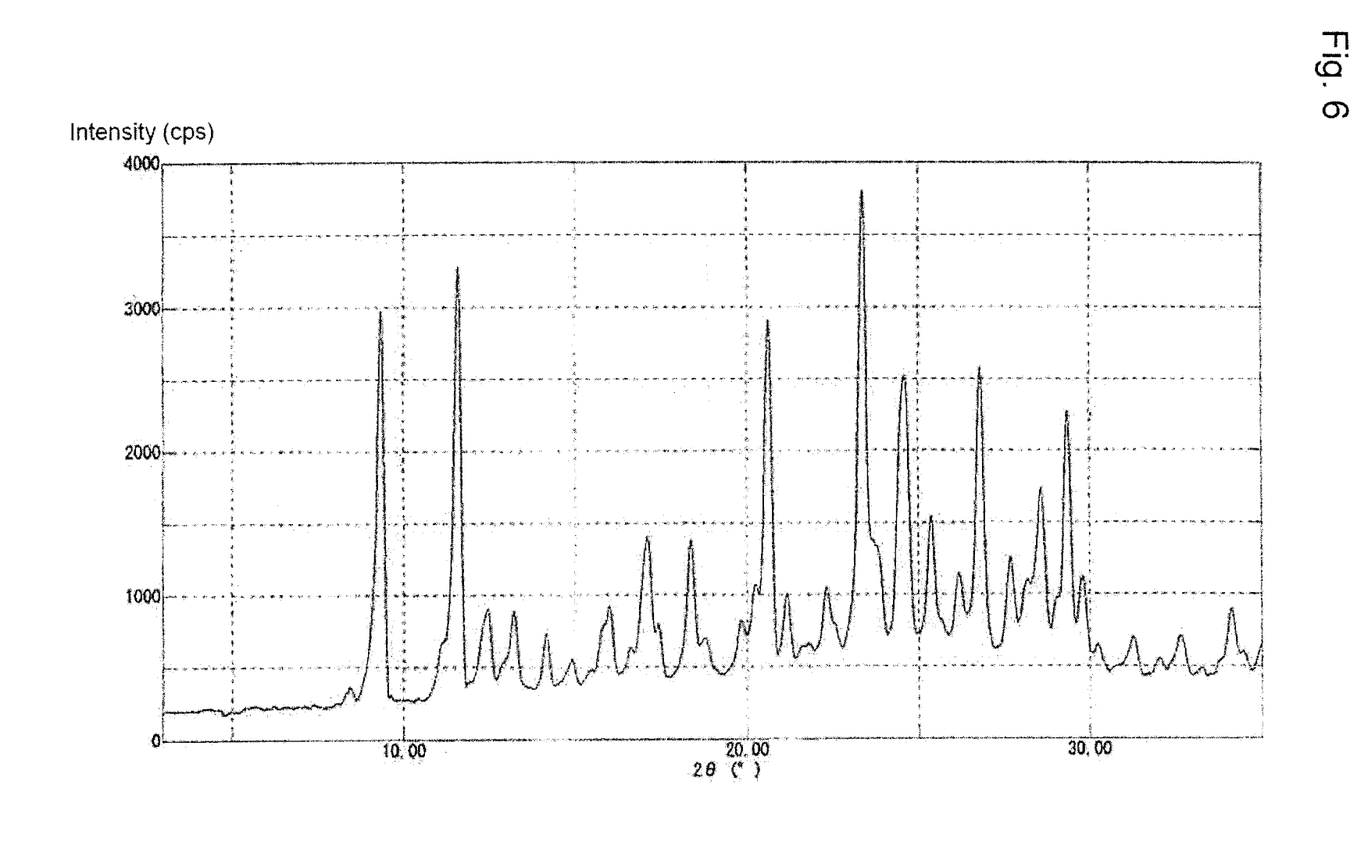
FIG. 6 is a chart of a powder X-ray diffraction spectrum of a crystal (Z type crystal) of the compound A obtained in Example 6, in which the vertical axis represents the intensity and the horizontal axis represents a diffraction angle (2θ(°)).

From the $^1$H-NMR data above, it was thus demonstrated that the crystal of the obtained compound A contains EtOH at a molar ratio of 8/10. The chart showing the results of the differential scanning calorimetry analysis (DSC analysis) and the chart of the powder X-ray diffraction spectrum of this crystal are shown in FIGS. 5 and 6, respectively.

The crystal (Z type crystal) of the compound A is a crystal which has peaks at 2θ) (°)=about 9.3, about 11.6, about 20.6, about 23.4, and about 29.4 in the powder X-ray diffraction using Cu as a radiation source. Further, this crystal (Z type crystal) of the compound A absorbed heat at around 102° C. in the differential scanning calorimetry analysis (DSC analysis).

Example 7

Production-2 of Z Type Crystal of Compound A

Under a nitrogen atmosphere, to a solution of 1.11 g of (2R)-2-hydroxypropanimidamide hydrochloride (1) in NMP (8 mL) were added 3.07 g of 3,4-dihydro-2H-pyran and 0.05 g of methanesulfonic acid at an inner temperature of 20° C. to 30° C., followed by stirring at the same temperature for 19 hours. To the reaction mixture were added 2 mL of AcOEt and 2.71 g of triethylamine at an inner temperature of 15° C. to 30° C., followed by stirring at an inner temperature of 0° C. to 10° C. for 5 minutes or longer (reaction liquid A). Under a nitrogen atmosphere, into another reaction vessel were added 4.00 g of 5-[3-(2,5-difluorophenyl)-2-(1,3-dihydro-2H-benzoimidazol-2-ylidene)-3-oxopropanoyl]-2-fluorobenzenesulfonyl chloride (3), 20 mL of AcOEt, and 22 mL of water, followed by stirring. The reaction liquid A as prepared earlier was added thereto at an inner temperature of 0° C. to 10° C., followed by washing with 2 mL of AcOEt and 2 mL of water, and stirring at an inner temperature of 20° C. to 30° C. for 1.5 hours. The reaction mixture was subjected to liquid separation at an inner temperature of 20° C. to 30° C., and the organic layer was washed sequentially with 16 mL of a 5% aqueous sodium hydrogen carbonate solution and 12 mL of a 20% aqueous sodium chloride solution. The obtained organic layer was concentrated to about 12 mL under reduced pressure, and 40 mL of AcOEt was added thereto, followed by concentrating to about 12 mL under reduced pressure (at an outer temperature of 40° C.). 4 mL of AcOEt and 40 mL of IPA were added thereto, followed by dropwise addition of 0.81 mL of a 2 M hydrogen chloride/IPA solution at an inner temperature of 20° C. to 30° C. The mixture was stirred at the same temperature for 7 hours and cooled to an inner temperature of 0° C. to 10° C. The reaction solution was added dropwise to a mixed liquid of 32 mL of AcOEt and 40 mL of a 2.5% aqueous sodium hydrogen carbonate solution at an inner temperature of 0° C. to 10° C., and washed with 8 mL of AcOEt. The organic layer was collected by filtration, and washed sequentially with 20 mL of a 5% aqueous sodium hydrogen carbonate solution and 20 mL of a 20% aqueous sodium chloride solution (at an inner temperature of 20° C. to 30° C.). The organic layer was concentrated to about 12 mL under reduced pressure, and then 40 mL of EtOH was added thereto, followed concentrating to about 16 mL under reduced pressure. 40 mL of EtOH was further added thereto, followed by concentrating to about 16 mL under reduced pressure (at an outer temperature of 40° C., the insoluble materials were precipitated). 32 mL of EtOH and 6 mL of water were added thereto at an inner temperature of 40° C. or lower, followed by warming to an inner temperature of 55° C. to 75° C. to dissolve the insoluble materials. 2 mg of Z type crystal of the compound A as a seed crystal was added thereto at an inner temperature of 45° C. to 55° C., followed by stirring at an inner temperature of 40° C. to 50° C. for 2 hours. 26 mL of water was added dropwise thereto at the same temperature for 1 hour, followed by stirring for 2 hours. Thereafter, the mixture was cooled to an inner temperature of 0° C. to 10° C. for 2 hours and stirred at the same temperature for 15 hours, and the precipitated crystal was collected by filtration, then washed with 20 mL of an EtOH/water mixed solution (1/1 (v/v)), and dried at 60° C. overnight under reduced pressure to obtain 3.92 g of the compound A as a crystal.

From the chart of the powder X-ray diffraction spectrum, it was confirmed that the crystal of the compound A thus obtained is of the same crystal type as the crystal of the compound A obtained Example 6 as described above.

Furthermore, the HPLC analysis results of the reaction mixture before crystallization of the compound A and/or the Z type crystal of the compound A obtained after crystallization are shown in Tables 3 and 4, respectively.

TABLE 3

Chemical Purity

| | Reaction mixture before crystallization | Z type crystal of the compound A obtained after crystallization |
|---|---|---|
| Compound A (retention time: about 11.1 minutes) | 95.64% | 98.28% |
| One diastereomer of compound (4) (retention time: about 21.6 minutes) | 0.34% | 0.31% |
| The other diastereomer of compound (4) (retention time: about 22.1 minutes) | 0.23% | 0.23% |
| Compound B (retention time: about 27.8 minutes) | 0.08% | 0.08% |

The numbers in the Table represent HPLC area percentages (%).

<HPLC Analysis Conditions>
The conditions are the same as in Example 3.

From Table 3, it was confirmed that in the present production process, the by-production of the compound B can be controlled to about 1/1200 or less relative to the compound A.

TABLE 4

Optical Purity

| | Z type crystal of the compound A obtained after crystallization |
|---|---|
| Compound A (retention time: about 27.1 minutes) | 99.64% |
| Enantiomer of compound A (retention time: about 19.1 minutes) | 0.05% |

The numbers in the Table represent HPLC area percentages (%).

<HPLC Analysis Conditions>
The conditions are the same as in Example 3.

From Table 4, it was confirmed that the racemization rate of the compound A is about 0.05%.

Preparation Example 1

Production of 1-(2,5-Difluorophenyl)-2-(1,3-dihydro-2H-benzoimidazol-2-ylidene)ethanone Under a nitrogen atmosphere, to a solution of 5.0 g of 2-methyl-1H-benzoimidazole and 12.44 g of triethylamine in THF (60 mL) was added 21.37 g of 2,5-difluorobenzoyl chloride at an inner temperature of 50° C. or lower, followed by stirring at an inner temperature of 60° C. to 70° C. for 3 hours. The reaction mixture was cooled to an inner temperature of 20° C. to 30° C., and then 6.92 g of morpholine was added thereto at an inner temperature of 20° C. to 50° C., followed by stirring at an inner temperature of 60° C. to 70° C. for 2 hours. 90 mL of water and 60 mL of MeCN were each added dropwise thereto over 30 minutes at an inner temperature of 40° C. to 50° C., followed by stirring at the same temperature for 1 hour. Thereafter, the mixture was cooled to an inner temperature of 0° C. to 10° C. for 1 hour or longer and stirred at the same temperature for 12 hours, and then the precipitated crystal was collected by filtration and washed sequentially with 15 mL of an MeCN/water mixed solution (2/1 (v/v)) and 25 mL of water.

The obtained crystal was suspended in 25 mL of MeCN and 50 mL of water, followed stirring at an inner temperature of 40° C. to 50° C. for 30 minutes and then stirring at an inner temperature of 20° C. to 30° C. for 1 hour. The crystal was collected by filtration, then washed with 25 mL of an MeCN/water mixed solution (17/33 (v/v)) and dried at 60° C. overnight under reduced pressure to obtain 9.66 g of 1-(2,5-difluorophenyl)-2-(1,3-dihydro-2H-benzoimidazol-2-ylidene)ethanone as a crystal.

The physicochemical data of the obtained compound are shown below.

$^1$H-NMR (DMSO-d6, 400 MHz): δ (ppm)=5.91 (1H, s), 7.11-7.16 (2H, m), 7.21-7.38 (4H, m), 7.53 (1H, brs), 7.55-7.61 (1H, m), 12.29 (1H, brs)
ESI-MS: m/z=273 ([M+H]$^+$)

Preparation Example 2

Production of 5-[3-(2,5-difluorophenyl)-2-(1,3-dihydro-2H-benzoimidazol-2-ylidene)-3-oxopropanoyl]-2-fluorobenzenesulfonyl chloride (3)

Under a nitrogen atmosphere, to a solution of 17.53 g of 3-(chlorosulfonyl)-4-fluorobenzoic acid in AcOiPr (90 mL) were added dropwise 12.24 g of thionyl chloride and 0.2 mL of DMF at an inner temperature of 50° C. or lower, followed by stirring at an inner temperature of 60° C. to 70° C. for 3 hours. The reaction mixture was concentrated under reduced pressure until the solvent was not evaporated any longer, and then azeotroped with 44 mL of AcOiPr twice (at an outer temperature of 30° C. to 40° C.).

The obtained residue was dissolved in 80 mL of THF, and 10.0 g of 1-(2,5-difluorophenyl)-2-(1,3-dihydro-2H-benzoimidazol-2-ylidene)ethanone and 3.72 g of N-methylmorpholine were sequentially added thereto at an inner temperature of 30° C. or lower, followed by stirring at an inner temperature of 55° C. to 65° C. for 3 hours.

To the reaction liquid were sequentially added 80 mL of methylisobutylketone and 140 mL of a 5% aqueous sodium hydrogen carbonate solution at an inner temperature of 5° C. to 15° C., followed by stirring at the same temperature for 1 hour and then carrying out liquid separation. To the organic layer was added 140 mL of a 5% aqueous sodium hydrogen carbonate solution at an inner temperature of 5° C. to 15° C., followed by stirring at the same temperature for 15 hours and then carrying out liquid separation. The organic layer was washed with 60 mL of a 20% aqueous sodium chloride solution and then concentrated to about 50 mL at an outer temperature of 30° C. to 40° C. under reduced pressure. 20 mL of toluene and 10.0 mg of a seed crystal of 5-[3-(2,5-difluorophenyl)-2-(1,3-dihydro-2H-benzoimidazol-2-ylidene)-3-oxopropanoyl]-2-fluorobenzenesulfonyl chloride (the compound of Reference Example 282 in Patent Document 1, which can be produced by the production method described in the document) were sequentially added thereto at an inner temperature of 20° C. to 30° C., followed by stirring at the same temperature for 4 hours. 100 mL of heptane was added dropwise at an inner temperature of 20° C. to 30° C. for 1 hour or longer, followed by stirring for 1 hour, then cooling to an inner temperature of −5° C. to 5° C., and stirring for 12 hours. The precipitated crystal was collected by filtration, then washed with 30 mL of a toluene/heptane mixed solution (1/1 (v/v)), and dried at 50° C. overnight under reduced pressure to obtain 16.12 g of 5-[3-(2,5-difluorophenyl)-2-(1,3-dihydro-2H-benzoimidazol-2-ylidene)-3-oxopropanoyl]-2-fluorobenzenesulfonyl chloride (3) as a crystal.

The physicochemical data of the compound (3) are shown below.

$^1$H-NMR (DMSO-d6, 400 MHz): δ (ppm)=6.68-6.78 (2H, m), 6.84-6.91 (1H, m), 6.92-6.97 (1H, m), 7.24-7.30 (3H, m), 7.68-7.74 (3H, m), 13.12 (2H, s)

ESI-MS: m/z=493 ([M+H]$^+$)

Comparative Example 1

According to the production process of Example 696 in Patent Document 1, (2R)-2-hydroxypropanimidamide hydrochloride was reacted with 5-[3-(2,5-difluorophenyl)-2-(1,3-dihydro-2H-benzoimidazol-2-ylidene)-3-oxopropanoyl]-2-fluorobenzenesulfonyl chloride. To the reaction liquid were added water and AcOEt to carry out a liquid separation operation, the organic layer was washed with a saturated aqueous sodium chloride solution, and then the solvent was evaporated under reduced pressure. The HPLC analysis results of the residue thus obtained in an amorphous state are shown below.

[Chemical Purity]
<HPLC Analysis Conditions>
The conditions are the same as in Example 3.
<HPLC Analysis Results>
Under the conditions above, it was demonstrated that the HPLC area percentages of the peak of the compound A and the peak of the compound B were 80.27% and 7.49%, respectively, and the compound B which is hardly removed without purification with columns was by-produced at a ratio of about 1/11 relative to the compound A.

[Optical Purity]
<HPLC Analysis Conditions>
The conditions are the same as in Example 3.
<HPLC Analysis Results>
Under the conditions above, it was demonstrated that the HPLC area percentages of the peak of the compound A and the peak of the enantiomer of the compound A were 90.15% and 1.44%, respectively, and the racemization rate of the compound A was 1.58%.

Further, the physicochemical data of the compound B are shown below.

$^1$H-NMR (DMSO-d6, 400 MHz): δ (ppm)=1.30 (3H, d, J=6.4 Hz), 4.87 (1H, q, J=6.4 Hz), 6.69-6.81 (2H, m), 6.86-6.92 (1H, m), 6.93-7.01 (2H, m), 7.02-7.12 (2H, m), 7.23-7.31 (5H, m), 7.53-7.60 (1H, m), 7.69-7.80 (7H, m), 8.24 (1H, s), 8.90 (1H, s), 13.19 (2H, s), 13.21 (2H, s)

ESI-MS: m/z=1001 ([M+H]$^+$)

From the results of Examples 3 and 7, and Comparative Example 1 (Supportive Tests of Production Methods described in Patent Document 1), it can be seen that in the production method of the present invention, the by-production of the compound B which is hardly removed without purification with columns is remarkably controlled, and the racemization of the compound A is also controlled. Accordingly, it is thought that the production method of the present invention is a production method suitable for industrial production required not to include a purification step by columns from the viewpoints of operability or cost.

Comparative Example 2

In Example 3, the racemization rate of the compound A obtained using a trimethylsilyl (TMS) group, a tert-butyldimethylsilyl (TBDMS) group, a tert-butyldiphenylsilyl (TBDPS) group, a dimethylphenylsilyl (DMPS) group, and a triisopropylsilyl (TIPS) group, which are representative protective groups for a hydroxyl group instead of a 2-tetrahydropyranyl group, as a protective group for a hydroxyl group of (2R)-2-hydroxypropanimidamide hydrochloride (1) in dichloromethane was investigated. Specifically, the compound (1) was reacted with 1.05 to 1.2 equivalents of the corresponding silyl chloride in the presence of 2.1 to 2.5 equivalents of triethylamine and 0.05 equivalents of 4-dimethylaminopyridine at room temperature, and then water was added thereto to carry out a liquid separation operation. The organic layer was concentrated under reduced pressure. The obtained residue was reacted with the compound (3) at room temperature and post-treated similarly to the Example 3. The organic layer was concentrated under reduced pressure. The obtained residue was treated with 1.2 equivalents of tetrabutylammonium fluoride and 1.2 equivalents of acetate at 0° C. in THF, and then water and AcOEt were added thereto to carry out a liquid separation operation. The organic layer was concentrated under reduced pressure, the obtained residue was analyzed by HPLC under the same conditions as in Examples 3 and 7, and the racemization rate of the obtained compound A was calculated from the HPLC area percentage. As a result, the racemization rate of the obtained compound A was each 4.16% to 4.22%, 0.60% to 0.65%, and 0.56% to 0.57%, the respectively, in the case of using a TBDMS group, a TBDPS group, and a TIPS group. Further, the TMS-protection of a hydroxyl group of the compound (1) becomes complicated in the reaction system, and thus, a DMPS-protection did not proceed and in any case, a compound having a desired hydroxyl group protected could not be obtained.

From the results of Examples 3 and 7 and Comparative Example 2, it can be seen that as a protective group for the hydroxyl group of the compound (1), the 2-tetrahydropyranyl group of the production method of the present invention is excellent from the viewpoint of control of racemization of the compound A.

INDUSTRIAL APPLICABILITY

According to the present invention, a production method for obtaining a compound of the formula (I) or a salt thereof at a high purity, which is suitable for industrial production. Further, a synthesis intermediate and a crystal of the compound of the formula (I), which are each useful in the production method, are provided.

The invention claimed is:
1. A method for producing a compound or a salt, hydrate, or solvate thereof, the method comprising:
deprotecting a 2-tetrahydropyranyl group from a compound (4) or a salt, hydrate, or solvate thereof, thereby obtaining a compound of formula (I) or a salt, hydrate, or solvate thereof:

wherein Me is a methyl group and THP is a 2-tetrahydropyranyl group.

2. The method of claim 1, wherein the compound (4) or salt, hydrate, or solvate thereof is obtained by a process comprising subjecting a compound (2) to sulfonyl amidination with a compound (3):

[Chem. 1]

thereby obtaining the compound (4) or salt, hydrate, or solvate thereof, wherein HCl is a hydrochloride salt.

3. The method of claim 2, wherein compound (2) is obtained by a process comprising 2-tetrahydropyranylation of compound (1):

4. The method of claim 1, wherein a free compound of formula (I) is obtained from the deprotecting.

5. The method of claim 1, wherein a salt of the compound of formula (I) is obtained from the deprotecting.

6. The method of claim 1, wherein a purity of the compound of formula (I) or the salt, hydrate, or solvate thereof is at least 93.72%.

7. The method of claim 1, wherein the compound of formula (I), or the salt, hydrate, or solvate thereof, is free of a compound B having a structure:

Compound B or
wherein a content of the compound B in the compound of formula (I) or the salt, hydrate, or solvate thereof is less than or equal to 0.32%.

* * * * *